(12) United States Patent
Bui et al.

(10) Patent No.: US 8,609,074 B2
(45) Date of Patent: Dec. 17, 2013

(54) METHODS FOR MAKING UP A KERATINOUS SUBSTRATE

(75) Inventors: Hy Si Bui, Piscataway, NJ (US); Chunhua Li, Scotch Plains, NJ (US); Jean-Thierry Simonnet, Mamtaroneck, NY (US); Xian Zhi Zhou, Leonia, NJ (US); Nicholas Stergios Lioutas, Philadelphia, PA (US)

(73) Assignee: L'Oreal, Paris (FR)

( * ) Notice: Subject to any disclaimer, the term of this patent is extended or adjusted under 35 U.S.C. 154(b) by 36 days.

(21) Appl. No.: 13/341,866

(22) Filed: Dec. 30, 2011

(65) Prior Publication Data

US 2013/0167859 A1  Jul. 4, 2013

(51) Int. Cl.
*A61Q 3/02* (2006.01)
*A61Q 1/00* (2006.01)
*A61Q 1/10* (2006.01)
*A61Q 5/00* (2006.01)

(52) U.S. Cl.
USPC ........... 424/61; 424/59; 424/70.11; 424/70.7; 424/401

(58) Field of Classification Search
None
See application file for complete search history.

(56) References Cited

U.S. PATENT DOCUMENTS

| | | |
|---|---|---|
| 4,272,620 A | 6/1981 | Ichimura |
| 4,287,335 A | 9/1981 | Ichimura |
| 4,339,524 A | 7/1982 | Ichimura et al. |
| 4,564,580 A | 1/1986 | Ichimura et al. |
| 4,777,114 A | 10/1988 | Ichimura et al. |
| 2006/0239946 A1* | 10/2006 | Samain et al. ................. 424/63 |
| 2007/0199161 A1* | 8/2007 | Pasquier et al. .................. 8/405 |

* cited by examiner

*Primary Examiner* — Jyothsna Venkat
(74) *Attorney, Agent, or Firm* — O'Brien Jones PLLC

(57) ABSTRACT

Disclosed herein are methods of making up and/or enhancing the appearance of a keratinous substrate comprising (1) forming a film on the keratinous substrate by applying to said keratinous substrate (a) a first cosmetic composition comprising at least one polyvinyl alcohol-styrylpyridinium polymer and (b) a second cosmetic composition comprising at least one complexing agent, and (2) exposing the film to radiation chosen from UV and visible light radiation.

17 Claims, No Drawings

METHODS FOR MAKING UP A KERATINOUS SUBSTRATE

FIELD OF THE DISCLOSURE

The disclosure relates to methods of making up and/or enhancing the appearance of a keratinous substrate comprising (1) forming a film on the keratinous substrate by applying to said keratinous substrate (a) a first cosmetic composition comprising at least one polyvinyl alcohol-styrylpyridinium polymer and (b) a second cosmetic composition comprising at least one complexing agent and (2) exposing the film to radiation chosen from UV and visible light radiation. Methods according to various embodiments of the disclosure may result in keratinous treatments that exhibit improved properties, such as improved water- and/or oil- and/or chemical-resistance, shine, adhesion, strength, and/or long wear.

BACKGROUND

Gel-based cosmetic compositions are known. For example, gel-based nail polishes have become increasingly popular in recent years, as they may provide improved properties over conventional nail polishes, such as extended wear and improved shine. However, consumers have raised safety concerns regarding the small molecules, such as the presence of photoinitiators and monomers in available gel-based nail polishes. In addition, gel-based nail polishes must be cured using UV radiation and can be difficult to remove. Furthermore, the application of gel-based nail polishes is expensive, time-consuming, and requires salon services for application and removal.

Thus, there is a desire in the cosmetic industry to provide consumers with safer and/or more convenient photo-curable cosmetic products that do not comprise small molecules such as photoinitiators, do not require curing with UV radiation, and/or exhibit improved ease of application and/or removal. In addition, it is desired that such photo-curable cosmetic products exhibit improved properties such as improved water- and/or oil- and/or chemical-resistance, shine, adhesion, strength, and long wear. As such, there is a continuous need to invent novel cosmetic compositions and methods of making up keratinous fibers which demonstrate one or more of said improved properties.

DESCRIPTION OF EXEMPLARY EMBODIMENTS

This disclosure relates, in various embodiments, to a method of making up and/or enhancing the appearance of a keratinous substrate comprising (1) forming a film on the keratinous substrate by applying to said keratinous substrate (a) a first cosmetic composition comprising at least one polyvinyl alcohol-styrylpyridinium polymer and (b) a second cosmetic composition comprising at least one complexing agent, and (2) exposing the film to radiation chosen from UV and visible light radiation.

Polyvinyl alcohol-styrylpyridinium ("PVA-SbQ") polymers have been widely used in various arts as photocrosslinkable materials due to their high photosensitivity and good storage stability. Upon exposure to UV or visible light radiation, PVA-SbQ polymers are capable of crosslinking via a 2+2 cycloaddition reaction without the use of a photoinitiator. However, the use of PVA-SbQ polymers in the cosmetic arts has been limited due to their highly hydrophilic nature. Thus, known cosmetic compositions comprising PVA-SbQ polymers may have less than satisfactory properties. For example, nail varnish compositions comprising PVA-SbQ may exhibit poor adhesion to the nail and/or may not be sufficiently water- and/or oil-resistant.

It has now been surprisingly discovered, however, that a film with improved cosmetic properties, such as improved water- and/or oil- and/or chemical-resistance, shine, adhesion, strength, and/or long wear may be obtained by applying to a keratinous substrate (a) a first cosmetic composition comprising at least one polyvinyl alcohol-styrylpyridinium polymer and (b) a second cosmetic composition comprising at least one complexing agent, and (2) exposing the resulting film to radiation chosen from UV and visible light radiation.

According to the disclosure, PVA-SbQ polymers useful in various embodiments may be chosen from polyvinyl alcohol polymers comprising at least one pendent styrylpyridinium group of formula (I):

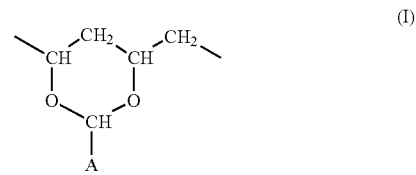

wherein A is chosen from:
(1) groups of formula (II):

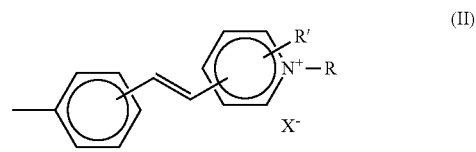

wherein R is chosen from hydrogen, alkyl groups, and hydroxyalkyl groups; R' is chosen from hydrogen and alkyl groups; and $X^-$ is an anion chosen from chloride, bromide, iodide, sulfates, methosulfates, perchlorates, phosphates, and sulfonates; and
(2) groups of formula (III):

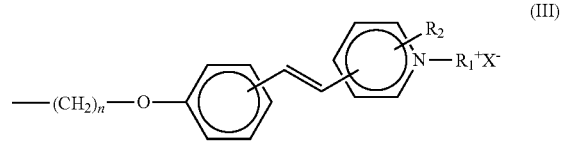

wherein $R_1$ is chosen from hydrogen, alkyl groups, and aralkyl groups; $R_2$ is chosen from hydrogen and alkyl groups; $X^-$ is an anion chosen from chloride, bromide, iodide, sulfates, methosulfates, perchlorates, phosphates, and sulfonates; and n is an integer ranging from 1 to 6.

By way of non-limiting example, PVA-SbQ polymers include those described in U.S. Pat. Nos. 4,272,620, 4,287,335, 4,339,524, 4,564,580, and 4,777,114, the disclosures of which are incorporated herein by reference in their entireties. For example, the at least one PVA-SbQ polymer may be chosen from polyvinyl alcohol polymers comprising at least one pendent styrylpyridinium group chosen from:
1-methyl-2-{m-(2,2-dimethoxyethoxy)-styryl}-pyridinium iodide, 1-methyl-2-{o-(2,2-dimethoxyethoxy)-styryl}-pyridinium iodide,
1-methyl-4-{p-(2,2-dimethoxyethoxy)-styryl}-pyridinium p-toluenesulfonate,
1-methyl-4-{p-(2,2-dimethoxyethoxy)-styryl}-pyridinium methosulfate,
1-methyl-2-(m-formylstyryl)-pyridinium p-toluenesulfonate,
1-methyl-2-(p-formylstyryl)-pyridinium p-toluenesulfonate,
1-methyl-2-(p-formylstyryl)-pyridinium iodide,
1-methyl-2-(p-formylstyryl)-pyridinium methosulfate,
1-methyl-4-(p-formylstyryl)-pyridinium p-toluenesulfonate,
1-methyl-4-(p-formylstyryl)-pyridinium methosulfate,
1-(2-hydroxyethyl)-2-(p-formylstyryl)-pyridinium chloride, and
1-carbamoylmethyl-4-(p-formylstyryl)-pyridinium chloride.

According to various embodiments of the disclosure, the at least one PVA-SbQ polymer may be chosen from poly(vinyl alcohol), N-methyl-4(4'-formylstyryl)pyridinium methosulfate acetal. Exemplary commercial PVA-SbQ polymer products that may be used in accordance with the disclosure include, but are not limited to, the product sold by Polysciences, Inc. under catalogue number 22570-75; and products sold by Murakami Co. Ltd. under the names EMULSION AD-V (poly(vinyl alcohol) with pendent pyridinium (and) ethylene/VA copolymer), EMULSION AD-V2 (poly(vinyl alcohol) with pendent pyridinium (and) ethylene/VA copolymer), and EMULSION AD-V2 PVA-SBQ (poly(vinyl alcohol) with pendent pyridinium).

In at least one exemplary embodiment, the molar ratio of PVA:SbQ in the at least one PVA-SbQ polymer may range from about 99.5:0.5 to about 85:15, for example, from about 99:1 to about 90:10, from about 98:2 to about 92:8, or from about 97:3 to about 95:5. According to another exemplary embodiment of the disclosure, the at least one PVA-SbQ polymer may have a molecular weight ranging from about 30,000 to about 100,000, for example, from about 40,000 to about 80,000, or from about 50,000 to about 70,000. In yet another exemplary embodiment, the at least one PVA-SbQ may have a degree of polymerization ranging from about 100 to about 2500, for instance, from about 200 to about 2000, from about 300 to about 1800, or from about 500 to 1000. In various exemplary embodiments, the at least one PVA-SbQ may have a degree of polymerization ranging from about 200 to about 800, for example, from about 300 to about 500.

According to at least certain embodiments, the at least one PVA-SbQ polymer is capable of crosslinking without the requirement of a photoinitiator. For example, without wishing to be bound, it is believed to be capable of crosslinking via a 2+2 cycloaddition reaction, upon exposure to UV or visible light radiation. For example, the at least one PVA-SbQ is capable of crosslinking, without a photoinitiator, upon exposure to radiation having a wavelength ranging from about 200 nm to about 800 nm, such as from about 250 nm to about 450 nm, or from about 265 nm to about 350 nm. In one exemplary embodiment, the at least one PVA-SbQ polymer is able to crosslink upon exposure to UV light radiation having a wavelength ranging from about 200 nm to about 400 nm. According to another exemplary embodiment, the at least one PVA-SbQ polymer is able to crosslink upon exposure to visible light radiation having a wavelength ranging from about 400 nm to about 800 nm.

In at least one exemplary embodiment, the at least one PVA-SbQ polymer may be present in the first cosmetic composition in an amount ranging from about 0.1% to about 40% by weight, such as from about 0.5% to about 30%, or from about 1% to about 20%.

As described herein, the second cosmetic composition comprises at least one complexing agent. According to various embodiments of the disclosure, the at least one complexing agent is capable of forming an intermacromolecular complex with the at least one PVA-SbQ polymer. In at least one exemplary embodiment, the at least one complexing agent is capable of crosslinking with the at least one PVA-SbQ polymer via hydrogen bonding.

In various embodiments of the disclosure, the at least one complexing agent may be chosen from, for example, hydroxycarboxylic acids, such as tartaric acid, gluconic acid, and citric acid; aminocarboxylic acids, such as ethylenediaminedisuccinic acid (EDDS), iminodisuccinic acid (IDS), hydroxyiminodisuccinic acid (HIDS), ethylenediaminetetraacetic acid (EDTA), methylglycinediacetic acid (MGDA), nitrilotriacetic acid (NTA), hydroxyethylenediaminetriacetic acid (HOEDTA), diethyleneaminepentaacetic acid (DPTA), diaminocyclohexanetetraacetic acid (CDTA), and diethylenetriaminepentaacetic acid (DTPA); polyacids, such as polyacrylic acid and polyaspartic acid; carboxypolysaccharides, such as carboxyethyl cellulose, chitosan, carboxymethyl chitosan, hyaluronic acid, alginate, propylene glycol alginate, pectin, carboxymethyl dextran, carboxymethyl chitosan, heparin, heparin sulfate, chondroitin sulfate, and polyuronic acids; hydroxyphosphonic acids, such as hydroxyethanediphosphonic acid; aminophosphonic acids, such as tris(aminomethyl)phosphonic acid, diethylenetriaminepentamethylenephosphonic acid, and ethylenediaminetetramethylenephosphonic acid; hydroxysulfonic acids; silanes such as aminopropyltriethoxysilane (APTES); polyamines; crown ethers; borates; silicates; derivatives thereof; and salts thereof with at least one cation chosen from alkali metals, alkaline earth metals, transition metals, amines, and ammonium.

According to various exemplary embodiments, the at least one complexing agent may be chosen from alkali metal salts of borates, such as sodium borate. In further exemplary embodiments, the at least one complexing agent may be chosen from alkali metal salts of silicates, such as sodium silicate. In further exemplary embodiments, the at least one complexing agent may be chosen from silanes, such as aminopropyltriethoxysilane.

According to other exemplary embodiments, the at least one complexing agent may be present in the second cosmetic composition in the form of an aqueous solution. In certain embodiments, the second cosmetic composition comprises at least one aqueous solution comprising the at least one complexing agent.

In various embodiments, the at least one complexing agent may be present in the second cosmetic composition in an amount ranging from about 0.1% to about 99% by weight, such as from about 1% to about 40%, or from about 5% to about 20%. In various exemplary embodiments, when the at least one complexing agent is sodium borate, the complexing agent may be present in the second cosmetic composition in an amount ranging from about 0.1% to about 10% by weight, for example, about 5% by weight. According to additional exemplary embodiments, when the at least one complexing agent is sodium silicate, the complexing agent may be present in the second cosmetic composition in an amount ranging from about 1% to about 40% by weight, for instance, from about 10% to about 20%. In yet further exemplary embodiments, when the at least one complexing agent is aminopropyltriethoxysilane, the complexing agent may be present in the second cosmetic composition in an amount ranging from about 1% to about 99% by weight, for example, from about 25 to about 75%.

According to various methods disclosed herein, the film formed on the keratinous substrate may subsequently be exposed to radiation chosen from UV and visible light radiation. In at least one exemplary embodiment, the film is exposed to radiation having a wavelength ranging from 200 nm to 800 nm. By way of non-limiting example, the film may be exposed to UV radiation having a wavelength ranging from about 200 nm to about 400 nm and/or visible light radiation having a wavelength ranging from about 400 nm to about 800 nm.

In further non-limiting embodiments, the film may be exposed to radiation for a time period ranging from about 0.5 minutes to about 60 minutes, for example, from about 1 minute to about 30 minutes, or from about 2 minutes to about 10 minutes.

One embodiment of the disclosure relates to methods of making up and/or enhancing the appearance of a keratinous substrate comprising (1) forming a film on a keratinous substrate by applying to said keratinous substrate (a) a first cosmetic composition comprising at least one polyvinyl alcohol-styrylpyridinium polymer and (b) a second cosmetic composition comprising at least one complexing agent chosen from sodium borate, sodium silicate, and aminopropyltriethoxysilane and (2) exposing the film to UV radiation, for example, radiation having a wavelength ranging from about 200 nm to about 400 nm.

Another embodiment of the disclosure relates to methods of making up and/or enhancing the appearance of a keratinous substrate comprising (1) forming a film on a keratinous substrate by applying to said keratinous substrate (a) a first cosmetic composition comprising at least one polyvinyl alcohol-styrylpyridinium polymer and (b) a second cosmetic composition comprising at least one complexing agent chosen from sodium borate, sodium silicate, and aminopropyltriethoxysilane and (2) exposing the film to visible light radiation, for example, radiation having a wavelength ranging from about 400 nm to about 800 nm.

Yet another embodiment of the disclosure relates to methods of making up and/or enhancing the appearance of a keratinous substrate comprising (1) forming a film on a keratinous substrate by applying to said keratinous substrate (a) a first cosmetic composition comprising at least one polyvinyl alcohol-styrylpyridinium polymer, and (b) a second cosmetic composition comprising an aqueous solution comprising sodium borate and (2) exposing the film to radiation chosen from UV and visible light radiation.

A further embodiment relates to methods of making up and/or enhancing the appearance of a keratinous substrate comprising (1) forming a film on a keratinous substrate by applying to said keratinous substrate (a) a first cosmetic composition comprising at least one polyvinyl alcohol-styrylpyridinium polymer, and (b) a second cosmetic composition comprising an aqueous solution comprising sodium silicate and (2) exposing the film to radiation chosen from UV and visible light radiation.

Another embodiment relates to methods of making up and/or enhancing the appearance of a keratinous substrate comprising (1) forming a film on a keratinous substrate by applying to said keratinous substrate (a) a first cosmetic composition comprising at least one polyvinyl alcohol-styrylpyridinium polymer, and (b) a second cosmetic composition comprising an aqueous solution comprising aminopropyltriethoxysilane and (2) exposing the film to radiation chosen from UV and visible light radiation.

A further embodiment relates to processes for forming a photo-curable film on a keratinous substrate comprising applying to said keratinous substrate (a) a first cosmetic composition comprising at least one polyvinyl alcohol-styrylpyridinium polymer and (b) a second cosmetic composition comprising at least one complexing agent.

According to various embodiments of the disclosure, the methods disclosed herein comprise a two-step application of the first and second compositions to the keratinous substrate. For instance, in one embodiment, a first composition as described is applied to the keratinous substrate and, subsequently, a second composition as described is applied to the first composition on the keratinous substrate. In another embodiment, a second composition as described is applied to the keratinous substrate and, subsequently, a first composition as described is applied to the second composition on the keratinous substrate. According to further embodiments, the first and second compositions may be applied to the keratinous substrate multiple times and in varying sequences. For example, a second composition may be applied to the keratinous substrate, followed by application of a first composition, followed by application of a second composition. Other embodiments apparent to those skilled in the art from both the description and general knowledge of making-up and/or treating keratinous substrates are also intended to be encompassed by this disclosure.

Without wishing to be bound by theory, it is believed that the at least one complexing agent forms hydrogen bonds with the hydroxy groups of the at least one PVA-SbQ polymer, thereby decreasing the hydrophilic effect of said hydroxy groups to produce a film with improved water resistance. It is also believed that the method comprising application of at least one PVA-SbQ polymer and at least one complexing agent to a keratinous substrate provides surprising and unexpected effects, imparting improved properties such as, for example, improved water- and/or oil- and/or chemical-resistance, shine, adhesion, strength, and/or long wear. It is further believed that, due to the hydrophilic nature of the PVA-SbQ polymer, films applied to the keratinous substrate in accordance with the methods of the disclosure will be easier to remove with conventional solvents. It should be noted, however, that methods according to the disclosure may not impart one or more of the above-referenced properties, yet such methods are intended to be within the scope of the disclosure.

In addition, other cosmetic ingredients may be included in the cosmetic compositions according to the disclosure. Such ingredients are known, and include but are not limited to solvents (including water), colorants, humectants, emulsifiers, surfactants, preservatives, fragrances, thickeners or texturizers, emollients, and additional film-formers, coalescents, and/or plasticizers. One of skill in the art will be able to select appropriate types and amounts of additional cosmetic ingredients, based on, for example, the type of cosmetic composition being formulated and the desired properties thereof. By way of example only, such additional cosmetic ingredients may be present in the compositions according to the disclosure in a combined amount ranging from about 10% to about 80% by weight, such as from about 15% to about 60%, from about 25% to about 40%, or from about 30% to about 35%.

Exemplary methods and processes contemplated according to the disclosure are intended for the make up and/or enhancement of keratinous substrates, such as the hair, skin, and nails. As such, the cosmetic compositions described herein include, but are not limited to, nail compositions (e.g. nail enamel), mascara compositions, make-up compositions (e.g. foundations), sunscreen compositions, and hair-care compositions (e.g. hair-styling compositions). In at least one embodiment, the cosmetic composition is a nail composition.

It is to be understood that the foregoing description and the following Examples are exemplary and explanatory only, and is not to be interpreted as restrictive of the disclosure. Moreover, it should be understood that various features and/or characteristics of differing embodiments herein may be combined with one another. It is therefore to be understood that numerous modifications may be made to the illustrative embodiments and that other arrangements may be devised without departing from the scope of the invention. Other embodiments will be apparent to those skilled in the art from consideration of the disclosure and practice of the various exemplary embodiments disclosed herein.

It is also to be understood that, as used herein the terms "the," "a," or "an," mean "at least one," and should not be limited to "only one" unless explicitly indicated to the contrary. Thus, for example, the use of "a PVA-SbQ polymer" is intended to mean at least one PVA-SbQ polymer.

Unless otherwise indicated, all numbers used in the specification and claims are to be understood as being modified in all instances by the term "about," whether or not so stated. It should also be understood that the precise numerical values used in the specification and claims form additional embodiments of the invention, and are intended to include any ranges which can be narrowed to any two end points disclosed within the exemplary ranges and values provided. Efforts have been made to ensure the accuracy of the numerical values disclosed herein. Any measured numerical value, however, can inherently contain certain errors resulting from the standard deviation found in its respective measuring technique.

EXAMPLES

The following Examples are intended to be non-restrictive and explanatory only, with the scope of the invention being defined by the claims.

Example 1

Nail Treatment Methods

Three simple nail treatments were prepared using the compositions listed in the following Table I. In comparative method 1, not in accordance with the disclosure, at least one PVA-SbQ polymer was applied to human nails, and no further compositions were applied. The treated nails were exposed to UV radiation for about 10 minutes. In inventive methods 2 and 3, at least one PVA-SbQ polymer was applied to human nails, followed by immersion of the nails into a second composition comprising at least one complexing agent for about 5 minutes. After removal of excess water, the treated nails were exposed to UV radiation for about 10 minutes.

TABLE I

Nail Treatments

| | METHOD 1 (comparative) | METHOD 2 (inventive) | METHOD 3 (inventive) |
|---|---|---|---|
| First Composition | PVA-SbQ (PolySciences 22570-75) | PVA-SbQ (PolySciences 22570-75) | PVA-SbQ (PolySciences 22570-75) |
| Second Composition | None | Sodium borate (5 wt % in water) | Sodium silicate (10 wt % in water) |

The nail treatments were each evaluated for shine, shine retention, and long wear. These observations are set forth in the following Table II. Shine was evaluated visually upon application and rated on a scale from 0 to 5, where 0 represents no shine and 5 represents high shine. Shine retention was evaluated visually after a period of about three days and rated on a scale from 0 to 5, where 0 represents no shine retention and 5 represents high shine retention. Wear was evaluated visually after a period of about three days and rated on a scale from 0 to 5, where 0 represents no adhesion to the nail surface and 5 represents high adhesion.

TABLE II

Evaluation of Nail Treatments

| | METHOD 1 (comparative) | METHOD 2 (inventive) | METHOD 3 (inventive) |
|---|---|---|---|
| Shine upon Application | 5 | 5 | 4 |
| Shine after 4 days | 0 | 5 | 4 |
| Wear after 4 days | 0 | 5 | 4 |

Nail treatments applied according to all methods exhibited satisfactory shine upon application. However, after three days of wear, the nail treatment applied according to comparative method 1 exhibited no adhesion to the nail surface, whereas the nail treatments applied according to inventive methods 2 and 3 exhibited excellent adhesion and long wear. Further, after three days of wear, the nail treatments applied according to inventive methods 2 and 3 exhibited excellent shine retention.

What is claimed is:

1. A method of making up and/or enhancing the appearance of the nails comprising:
   (1) forming a film on the nails by applying to the nails:
      (a) a first nail composition comprising at least one polyvinyl alcohol-styrylpyridinium polymer, and
      (b) a second nail composition comprising at least one complexing agent, and
   (2) exposing the film to radiation chosen from UV and visible light radiation;
   wherein the at least one polyvinyl alcohol-styrylpyridinium polymer is chosen from polyvinyl alcohol polymers comprising at least one pendent styrylpyridinium group of formula (I):

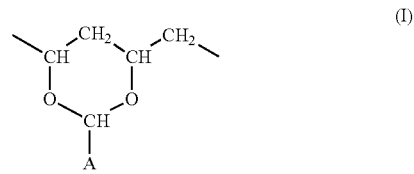

wherein A is chosen from:
(1) groups of formula (II):

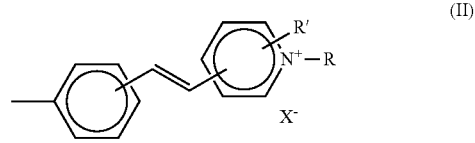

wherein R is chosen from hydrogen, alkyl groups, and hydroxyalkyl groups; R' is chosen from hydrogen and alkyl groups; and X⁻ is an anion chosen from chloride, bromide, iodide, sulfates, methosulfates, perchlorates, phosphates, and sulfonates; and
(2) groups of formula (III):

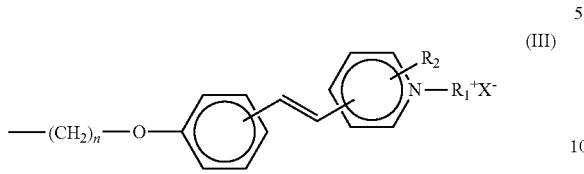

wherein $R_1$ is chosen from hydrogen, alkyl groups, and aralkyl groups; $R_2$ is chosen from hydrogen and alkyl groups; $X^-$ is an anion chosen from chloride, bromide, iodide, sulfates, methosulfates, perchlorates, phosphates, and sulfonates; and n is an integer ranging from 1 to 6; and
wherein the at least one complexing agent is chosen from tartaric acid, gluconic acid, citric acid, polyacrylic acid, polyaspartic acid, carboxyethyl cellulose, chitosan, carboxymethyl chitosan, hyaluronic acid, alginate, propylene glycol alginate, pectin, carboxymethyl dextran, heparin, heparin sulfate, chondroitin sulfate, polyuronic acids, sodium borate, sodium silicate, and aminopropyltriethoxysilane.

2. The method of claim 1, wherein the second nail composition is applied subsequent to the first nail composition.

3. The method of claim 1, wherein the at least one polyvinyl alcohol-styrylpyridinium polymer is poly(vinyl alcohol), N-methyl-4(4'-formylstyryl)pyridinium methosulfate acetal.

4. The method of claim 1, wherein the ratio of polyvinyl alcohol:styrylpyridinium in the at least one polyvinyl alcohol-styrylpyridinium polymer ranges from about 99:1 to about 90:10.

5. The method of claim 1, wherein the at least one polyvinyl alcohol-styrylpyridinium polymer is present in the first nail composition in an amount ranging from about 0.5% to about 30% by weight.

6. The method of claim 1, wherein the at least one complexing agent is chosen from sodium borate, sodium silicate, and aminopropyltriethoxysilane.

7. The method of claim 1, wherein the second nail composition comprises at least one aqueous solution comprising at least one complexing agent.

8. The method of claim 1, wherein the at least one complexing agent is present in the second nail composition in an amount ranging from about 0.1% to about 40% by weight.

9. The method of claim 1, wherein the film is exposed to UV radiation having a wavelength ranging from about 200 nm to about 400 nm.

10. The method of claim 1, wherein the film is exposed to visible light radiation having a wavelength ranging from about 400 nm to about 800 nm.

11. The method of claim 1, wherein the film is exposed to radiation for a time period ranging from about 1 minute to about 30 minutes.

12. A method of making up and/or enhancing the appearance of the nails comprising:
(1) forming a film on the nails by applying to the nails:
(a) a first nail composition comprising at least one polyvinyl alcohol-styrylpyridinium polymer, and
(b) a second nail composition comprising at least one aqueous solution comprising at least one complexing agent chosen from sodium borate, sodium silicate and aminopropyltriethoxysilane, and
(2) exposing the film to radiation chosen from UV and visible light radiation;

wherein the at least one polyvinyl alcohol-styrylpyridinium polymer is chosen from polyvinyl alcohol polymers comprising at least one pendent styrylpyridinium group of formula (I):

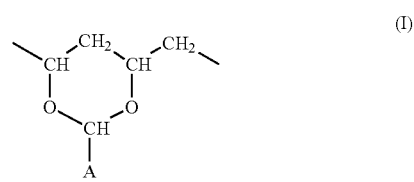

wherein A is chosen from:
(1) groups of formula (II):

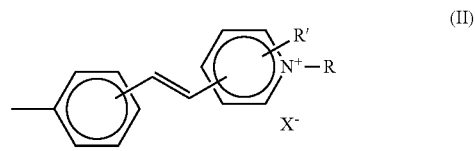

wherein R is chosen from hydrogen, alkyl groups, and hydroxyalkyl groups; R' is chosen from hydrogen and alkyl groups; and $X^-$ is an anion chosen from chloride, bromide, iodide, sulfates, methosulfates, perchlorates, phosphates, and sulfonates; and
(2) groups of formula (III):

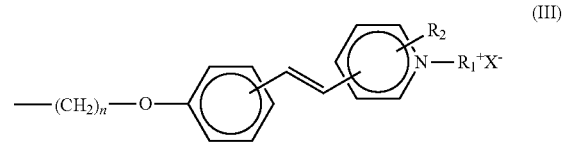

wherein $R_1$ is chosen from hydrogen, alkyl groups, and aralkyl groups; $R_2$ is chosen from hydrogen and alkyl groups; $X^-$ is an anion chosen from chloride, bromide, iodide, sulfates, methosulfates, perchlorates, phosphates, and sulfonates; and n is an integer ranging from 1 to 6.

13. A process for forming a photo-curable film on the nails, said process comprising applying to the nails:
(a) a first nail composition comprising at least one polyvinyl alcohol-styrylpyridinium polymer, and
(b) a second nail composition comprising at least one complexing agent;
wherein the at least one polyvinyl alcohol-styrylpyridinium polymer is chosen from polyvinyl alcohol polymers comprising at least one pendent styrylpyridinium group of formula (I):

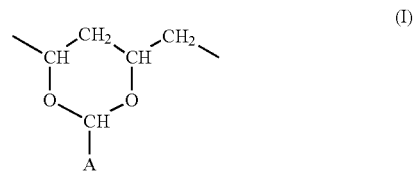

wherein A is chosen from:
(1) groups of formula (II):

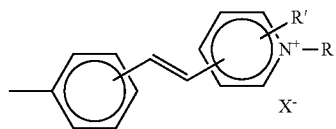

wherein R is chosen from hydrogen, alkyl groups, and hydroxyalkyl groups; R' is chosen from hydrogen and alkyl groups; and X⁻ is an anion chosen from chloride, bromide, iodide, sulfates, methosulfates, perchlorates, phosphates, and sulfonates; and
(2) groups of formula (III):

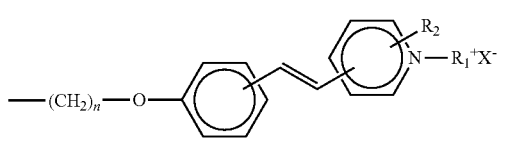

wherein $R_1$ is chosen from hydrogen, alkyl groups, and aralkyl groups; $R_2$ is chosen from hydrogen and alkyl groups; X⁻ is an anion chosen from chloride, bromide, iodide, sulfates, methosulfates, perchlorates, phosphates, and sulfonates; and n is an integer ranging from 1 to 6; and wherein the at least one complexing agent is chosen from tartaric acid, gluconic acid, citric acid, polyacrylic acid, polyaspartic acid, carboxyethyl cellulose, chitosan, carboxymethyl chitosan, hyaluronic acid, alginate, propylene glycol alginate, pectin, carboxymethyl dextran, heparin, heparin sulfate, chondroitin sulfate, polyuronic acids, sodium borate, sodium silicate, and aminopropyltriethoxysilane.

14. The process of claim 13, wherein the second nail composition is applied subsequent to the first nail composition.

15. The process of claim 13, wherein the at least one polyvinyl alcohol-styrylpyridinium polymer is poly(vinyl alcohol), N-methyl-4(4'-formylstyryl)pyridinium methosulfate acetal.

16. The process of claim 13, wherein the at least one complexing agent is chosen from sodium borate, sodium silicate, and aminopropyltriethoxysilane.

17. The process of claim 13, wherein the second nail composition comprises at least one aqueous solution comprising at least one complexing agent.

\* \* \* \* \*

UNITED STATES PATENT AND TRADEMARK OFFICE
CERTIFICATE OF CORRECTION

PATENT NO. : 8,609,074 B2
APPLICATION NO. : 13/341866
DATED : December 17, 2013
INVENTOR(S) : Hy Si Bui et al.

Page 1 of 1

It is certified that error appears in the above-identified patent and that said Letters Patent is hereby corrected as shown below:

On the title page, item (75) Inventors: Please change "Mamtaroneck" to -- Mamaroneck --.

Signed and Sealed this
Eleventh Day of March, 2014

Michelle K. Lee
*Deputy Director of the United States Patent and Trademark Office*